United States Patent

Brisdon et al.

[11] Patent Number: 4,900,845
[45] Date of Patent: Feb. 13, 1990

[54] MOIETY FOR SELECTIVE SEPARATION

[75] Inventors: Brian J. Brisdon; Richard England; Sera S. Abed-Ali, all of Bath, England

[73] Assignee: National Research Development Corporation, London, England

[21] Appl. No.: 147,992

[22] Filed: Jan. 25, 1988

[30] Foreign Application Priority Data

Feb. 5, 1987 [GB] United Kingdom ............... 8702569

[51] Int. Cl.$^4$ ............................................. C07D 323/00
[52] U.S. Cl. ..................................... 549/352; 549/353
[58] Field of Search ............................... 549/352, 353

[56] References Cited

U.S. PATENT DOCUMENTS 4,474,963 10/1984 Gokel ................................. 549/353

FOREIGN PATENT DOCUMENTS 1377280 2/1988 European Pat. Off. ............ 549/352
0279557 8/1988 European Pat. Off. ............ 549/352

Primary Examiner—Richard L. Raymond
Assistant Examiner—Amelia A. Owens
Attorney, Agent, or Firm—Nixon & Vanderhye

[57] ABSTRACT

New C-substituted crown ethers such as

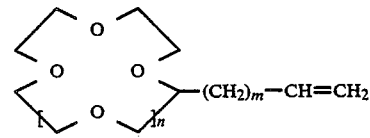

are made by reacting a 1,2-diol (chain length m+4) with $ClCH_2-(CH_2-O-CH_2-)_{n+1}CH_2Cl$.

These compounds have a stronger affinity for secondary amines than for tertiary amines and therefore may be used to separate mixtures, especially when attached to polysiloxane backbones or substrates via their unsaturated bond.

3 Claims, No Drawings

MOIETY FOR SELECTIVE SEPARATION

This invention relates to a moiety useful in selective separation of amines, to a separant compound incorporating the moiety, and to a membrane or liquid or solid comprising said compound in polymer form. The invention further relates to a method of synthesising the said moiety, and to a separation process using the moiety, compound or membrane.

The selective separation of amines is useful in for example the synthesis of several groups of drug molecules. Thus norcodeine, a secondary amine, could be synthesised from codeine, a tertiary amine (viz. N-methyl norcodeine), but this reaction is often difficult to achieve selectively with good yield by chemical means. Microbial N-dealkylation processes using Cunninghamella sp. on codeine readily produce norcodeine and formaldehyde under fermenter conditions, and although analytical-scale HPLC can effectively monitor the reaction, in full-scale production the chemical and physical similarity of the products and reactants causes a separation problem, which must be solved before bioconversions of this type become commercially possible.

A known solution to this separation problem lies in the use of chemical receptors, capable of molecular recognition, which preferentially complex protonated norcodeine, so forming a basis for its separation. Of the various types of receptor molecules available, crown ethers, such as 1,4,7,10,13,16-hexa-oxa-cyclo-octadecane (viz. 18-crown-6), are known to complex $RNH_3$ cations, whereas the smaller crown diaza-12-crown-4 (viz. 1,7-dioxa-4,10-diaza-cyclododecane) is known to bond strongly to $R_2NH_2$ cations, but not to $R_3NH$ cations. This ether so bonded is inferred to be:

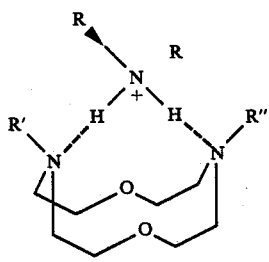

(I)

Furthermore, this receptor is easily derivatised and hence it has been proposed to attach it to a liquid polymer, in order that a continuous liquid-liquid extraction procedure might be developed. We have, however, now found this attachment step to be a major obstacle, and we have further found that other receptors are suitable and indeed preferable, such as the oxa analogue of the above, viz. 12-crown-4-ether (i.e. 1,4,7,10-tetraoxa-cyclododecane);

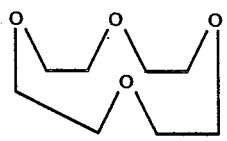

(II)

However, 12-crown-4-ether cannot be directly attached to a support and is difficult to modify chemically.

The present invention is 1,4,7,10-tetraoxa-2-alkenyl-cyclododecane, 1,4,7,10,13-pentaoxa-2-alkenyl-cyclopentadecane and 1,4,7,10,13,16-hexaoxa-2-alkenyl-cyclooctadecane.

The present invention is also the corresponding alkenyl moieties, for attachment to carriers. Thus, the invention also consists in a carrier providing one or more alkylene-polyoxa-cycloalkane groups derived from the foregoing compounds; the groups may be bonded to silicon atoms, which may be part either of a siloxane or of a silica particle. The invention therefore further extends to a siloxane (usually a polysiloxane, i.e. having 3 or more silicons) having this moiety as a substituent. The substituted polysiloxane may be in the form of a membrane. The alkenyl group may be $C_3$ to $C_6$ and may be omega-alkenyl such as 1-propen-3-yl or 1-hexen-6-yl, or indeed the double bond need not be at the distal (omega) end; the alkenyl group may be alkyl- or aryl-substituted.

Further according to the present invention, a method of synthesising the said alkenyl cycloalkane and the alkenyl moiety comprises linking the two oxygen atoms of an unsaturated 1,2-diol (made e.g. by hydroxylating the 1 and 2 positions of 1,7-octadiene), with a 3,6-dioxaoctamethylene bridge using an alpha, omega-substituted (e.g. halo e.g. chloro-substituted) ethoxy ethyl ether, e.g. 1,2-bis(2-chloroethoxy)ethane, with interpolated ethoxy groups for making larger cycloalkanes, and (for attaching the moiety to a carrier) opening the remaining unsaturated bond. The ether may be considered as $X-CH_2CH_2OCH_2[(CH_2)O(CH_2)]_nCH_2-Y$ where X and Y are the same or different substituents, and n=1, 2 or 3.

This opening may be effected by an agent such as chloroplatinic acid, and may be such as to bond the moiety to a substrate such as a column-packing bead (e.g. of silica or a siloxane, usually a polysiloxane, i.e. having 3 or more silicons. The thus-substituted substrate may be in the form of a membrane or a liquid separant or a solid separant. The substituted carrier may be used in the separation of secondary from tertiary amines, such as norcodeine from codeine. The norcodeine held by the substituted substrate may be stripped from it in a yield exceeding 95% by simply changing the pH.

As already alluded to, efficient downstream processing is a major problem in many of the increasingly complex chemical and biochemical processes of commercial interest. Liquid polymers, functionalised with suitably designed receptor groups capable of molecular recognition, suggest themselves as extractants for certain products.

Advantages of linear polysiloxanes include the ready commercial availability of the polymers themselves (e.g. dimethylsiloxane polymers as silicone fluids) and the low toxicity, high heat stability, high oxidation resistance, low vapour pressure, resistance to biodegradation, high flash points and immiscibility with water exhibited by this class of material. In addition, specific functionalities can be introduced in a reproducible and controlled manner via known chemical procedures, yielding polymers of the type shown below, where L is a functional group

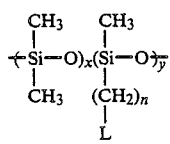

(III)

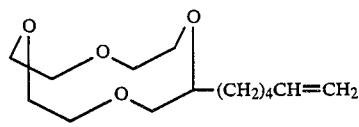

(VI)

Noting that the dimethylsiloxane groups are hydrophobic and the methylalkylene-siloxane groups may be rendered hydrophilic, varying the ratio x:y, and the total molecular weight of the polymer, alters many of the physical properties of the fluid, such as viscosity, organic solvent miscibility, water miscibility and chemical stability. By introducing specific ligating groups L, these fluids are capable of acting as selective extractants for specific water-soluble substrates. Thus these materials may be regarded as the fluid equivalent of affinity chromatography columns, in that the active sites are polymer-attached and cannot therefore be lost to the aqueous phase.

This technique may therefore by applied to liquid/liquid extraction, using crown-ether functionalised polysiloxanes to selectively extract N-demethylated drug molecules formed in bioconversion process, the extraction being able to be continuously performed in the reaction vessel even while the reaction is in progress, as exemplified by

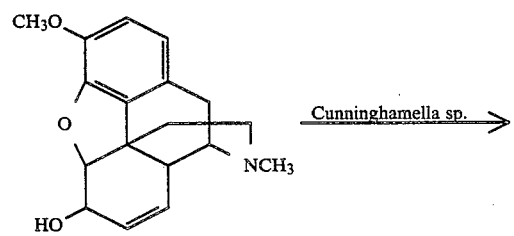

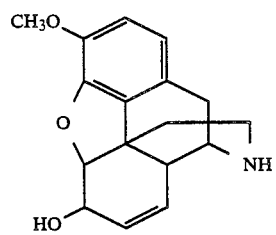

(IV)

The invention will now be described by way of example.

Under acidic conditions, only secondary amine salts are strongly complexed by 12-crown-4, compound (II), which thus forms the basis of an efficient solvent extraction process for the removal of the product of bioconversion (IV), protonated norcodeine, by extraction into a crown-ether functionalised liquid polysiloxane medium.

As (II) cannot be directly attached to a support, and is difficult to modify chemically, a new route according to the invention is described to the new compound 1,4,7,10-tetraoxa-2-(1-hexen-6-y1)-cyclododecane (VI) in order that polysiloxane attached 12-crown-4 derivatives can be prepared, and analogously the corresponding propenyl compounds and 15-crown-5 and 18-crown-6.

This can be produced easily according to the invention, at low cost from inexpensive starting materials. and it can be attached to polysiloxanes to make Polymer (III) (where L is crown) as will be described.

Polymer (III) was made with various ratios x:y, i.e. various ratios of hydrophobic $Me_2SiO$ units to hydrophilic $MeSi(O)(CH_2)_n$-crown units in order to vary the water solubility of the polymer. The values of x and y can be freely varied. Preferably $y/(x+y+2)$ is from 2% to 10%, otherwise there will be too few or too many functional groups for best effects. Preferably $x+y$ is from 1 to 1200 preferably at least 3, more preferably at least 15, most preferably at least 28 such as at least 50. Preferably $x+y$ is up to 1000, more preferably up to 500, most preferably up to 100, otherwise the polymer will either be rather soluble for use as an aqueous extractant or rather viscous, although these effects of varying $x+y$ can be partially compensated by varying $y/x$ in the same sense.

In particular, the polymer VII was made in four versions, VIIa, VIIb, VIIc and VIId.

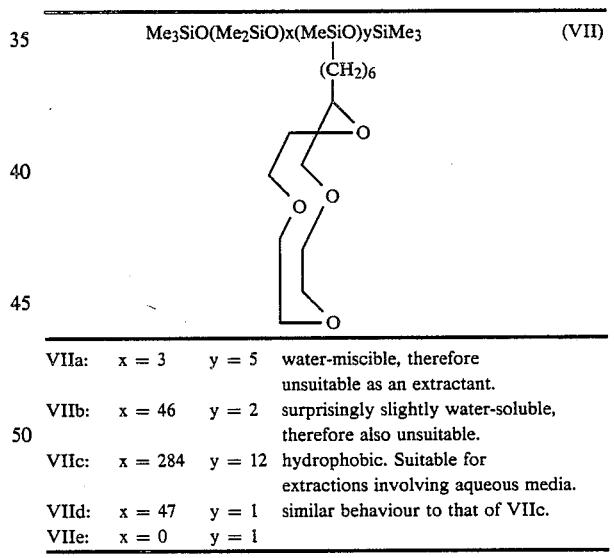

| | | | |
|---|---|---|---|
| VIIa: | x = 3 | y = 5 | water-miscible, therefore unsuitable as an extractant. |
| VIIb: | x = 46 | y = 2 | surprisingly slightly water-soluble, therefore also unsuitable. |
| VIIc: | x = 284 | y = 12 | hydrophobic. Suitable for extractions involving aqueous media. |
| VIId: | x = 47 | y = 1 | similar behaviour to that of VIIc. |
| VIIe: | x = 0 | y = 1 | |

The synthetic procedure was as follows:

1,4,7,10-tetraoxa-2-(1-hexen-6-y1)-cyclododecane, compound VI, was readily prepared by the two stage process outlined below, in a yield of 18%.

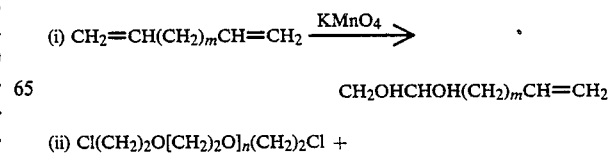

-continued $$CH_2OHCHOH(CH_2)_mCH=CH_2$$
$$\downarrow \text{dried } LiClO_4$$

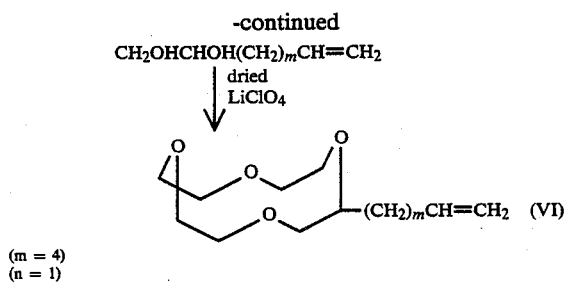

(m = 4)
(n = 1)

Note that m could be 0, 1, 2 or 3 instead. In place of one or both —Cl substituents, —CH$_2$-paraphenylene-SO$_2$ could be used. The function of the Li$^+$ is as a template around which the crown can form to the right size. For n=2, Na$^+$ would be suitable in the form of NaOH, and for n=3, elemental K.

Linear byproducts are in the main volatile and are removed by boiling them off.

For n=1 and 2, the minimum possible amount of dimethylsulphoxide was used as the solvent for stage (ii), (for n=3 tetrahydrofuran) held at 110° C. for at least 48 hours.

Then, 12-crown-4 functionalised polysiloxane Compound (V1) was linked to a 50-long polysiloxane chain following this route, no solvent being used:

(i) Me$_3$SiO(Me$_2$SiO)$_{46}$(MeHSiO)$_2$SiMe$_3$ + (VI)
$$\downarrow H_2PtCl_6$$
Me$_3$SiO(Me$_2$SiO)$_{46}$(MeSiO)$_2$SiMe$_3$

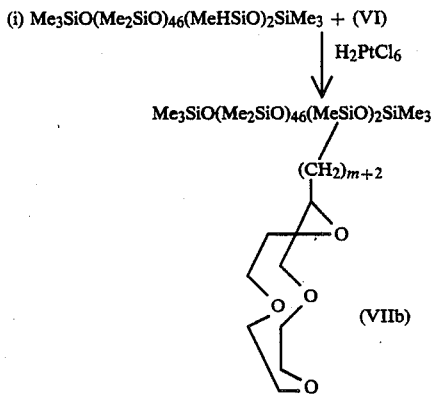

(VIIb)

Repeating the previous synthesis where n=2 and n=3 gave, instead of Compound (VI), the compounds CH$_2$=CH(CH$_2$)$_4$—15-crown-5 and CH$_2$=CH(CH$_2$)$_4$—18-crown-6 respectively. Changing the value of m changes the alkenyl chain. In particular, the compound m=1 (e.g. CH$_2$=CH—CH$_2$—15-crown-5) was useful. These crown compounds could also be attached to a linear polysiloxane moiety as described for compound (VIIb). Such materials have considerable potential for the selective complexation and extraction or transport of, for example, ionic metal ions of a specific size.

Repeating this synthesis with a deficiency of Compound (VI) leaves spare MeHSiO groups, of which the Si—H bond can be cleaved either to cross-link with other like Si groups using e.g. a tin catalyst to form a membrane or to bond the material to a solid substrate e.g. of silica.

Reactions of solutions of the crown ether derivative (II), (V) and (VI) with piperidinium, N-methyl-piperidinium, protonated norcodeine or protonated codeine (see (IV)) were investigated under a range of conditions. Spectroscopic studies revealed that strong complexation occurred between secondary amine salts and each of the crown ether derivatives and stable 1:1 adducts could be isolated from both hydroxylic and non-hydroxylic solvents. These adducts were fully characterised and spectral changes associated with NH$_2$ stretching modes (infrared) and NH$_2$ proton chemical shifts ($^1$H n.m.r.) indicated that complexations occurred via this functionality in all cases. On recrystallisation of protonated amine complexes of (V) several times from dichloromethane-cyclohexane mixtures, amine was slowly lost until pure, crystalline protonated diazo-12-crown-4 perchlorate was formed as the final product.

At concentrations of 10$^{-3}$-10$^{-4}$ molar (values typical of those found in downstream products from the fermenter process (IV)), only protonated norcodeine is strongly complexed and extracted from clear equimolar mixtures of codeine and norcodeine present as their perchlorate salts (Table 1).

TABLE 1

| | Single extraction* of equimolar (10$^{-4}$ M) mixtures of codeine and norcodeine | | |
|---|---|---|---|
| Polymer | Solvent | % norcodeine extracted by polymer | % codeine extracted by polymer |
| (VIIb) | MeOH | 17 | not detectable |
| (VIId) | MeOH | 44 | not detectable |
| (VIIc) | MeOH | 50 | not detectable |
| (VIIc) | H$_2$O | 25** | not detectable |

*determined by HPLC following extraction using equal volumes of extractant and amine solution, except for VIIb where volume ratios were 1:2
**recovered in about 95% yield from the polymer by extraction with 2 M methanolic NaOH solution Recovery of norcodeine was almost quantitative following extraction of the norcodeine containing polymer by methanolic NaOH solution.

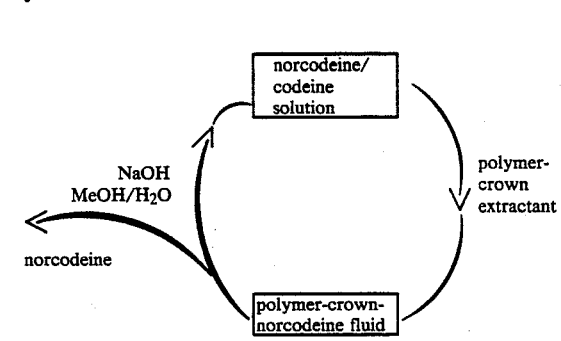

Throughout these operations the polymer (VII) and the norcodeine containing polymer remained as mobile liquids suitable for manipulation and use in a single or multistage extraction system.

It is appropriate to recall that the majority of inorganic membranes consist of finely porous inorganic solids. Conversely, the majority of synthetic polymer membranes are completely organic in origin, and as such show limited stability at high temperatures and in organic solvents. It is advantageous to combine the ease of fabrication, synthetic variability and cheapness of organic membranes with the thermal stability, solvent resistance and chemical inertness of inorganic materials. Of the possible materials with an inorganic backbone which might profitably be employed as polymer membranes, polysiloxanes —RR'Si—O—SiRR'—O—SiRR'—O— (R=R'=alkyl or aryl) appear the most appropriate in view of their ready availability (basis of silicones), stability and known chemistry, and this is exploited in the present invention. Selective modification of a restricted number of silicon centres in polydimethylsiloxanes should give a measure of control over both the permeability and selectivity of this type of material. but such a modification is extremely difficult to achieve on commercially available materials. However, in J.Chem.Soc.Dalton Trans 1985 p 2191 (Brisdon and Watts) synthetic procedures for a wide range of organofunctional methylsiloxanes are described. Copolymerisation of cyclic polydimethylsiloxanes with these materials provides an entry into organofunctional siloxanes of type (III) above in which the ratio x:y can be controlled precisely, so yielding polymers with a wide spectrum of chemical and physical characteristics. The mechanical properties and porosities of heteropolysiloxane membranes (heteropolysiloxanes=-polysiloxanes containing different alkyl or aryl silicon substituents and/or inorganic additives) are now known to be dependent upon the type and frequency of the organic group, the presence of inorganic additives, and the preparative method used to synthesise the membrane.

Thus these synthetic techniques are available for systematic modification of high permeability polydimethylsiloxanes to make a siloxane tailored to given requirements.

More generally, these siloxanes may form liquid-extraction (a) membrane—the material being cross-linked to itself;

(b) liquids; or (c) solids—the siloxane being adsorbed or cross-linked to a surface.

We claim:

1. 1,4,7,10-tetraoxa-2-$C_3$–$C_6$alkenyl-cyclododecane.

2. 1,4,7,10,13-pentaoxa-2-$C_3$–$C_6$alkenyl-cyclopentadecane.

3. 1,4,7,10,13,16-hexaoxa-2-$C_3$–$C_6$alkenyl-cyclooctadecane.

* * * * *